United States Patent
Tanaka et al.

(10) Patent No.: US 10,976,326 B2
(45) Date of Patent: Apr. 13, 2021

(54) SENSOR

(71) Applicant: KYOCERA CORPORATION, Kyoto (JP)

(72) Inventors: Hiroyasu Tanaka, Kyoto (JP); Yasutaka Ohashi, Kizugawa (JP); Hiroshi Katta, Kashihara (JP)

(73) Assignee: KYOCERA CORPORATION, Kyoto (JP)

( * ) Notice: Subject to any disclaimer, the term of this patent is extended or adjusted under 35 U.S.C. 154(b) by 346 days.

(21) Appl. No.: 15/191,435

(22) PCT Filed: Dec. 26, 2014

(86) PCT No.: PCT/JP2014/084515
§ 371 (c)(1),
(2) Date: Jun. 23, 2016

(87) PCT Pub. No.: WO2015/099123
PCT Pub. Date: Jul. 2, 2015

(65) Prior Publication Data
US 2016/0327575 A1    Nov. 10, 2016

(30) Foreign Application Priority Data
Dec. 26, 2013 (JP) ............................. JP2013-269211

(51) Int. Cl.
*G01N 33/72* (2006.01)
*C12Q 1/00* (2006.01)
(Continued)

(52) U.S. Cl.
CPC ............ *G01N 33/726* (2013.01); *B01L 3/502* (2013.01); *B01L 3/502715* (2013.01);
(Continued)

(58) Field of Classification Search
CPC ............... G01N 33/726; G01N 33/723; G01N 33/48785; G01N 33/558; G01N 33/5438;
(Continued)

(56) References Cited

U.S. PATENT DOCUMENTS 7,942,568 B1 *  5/2011  Branch ............... B01F 11/0266
                                                            366/127
2002/0146754 A1  10/2002  Kitawaki et al.
(Continued)

FOREIGN PATENT DOCUMENTS

EP       2158968 A1    3/2010
EP       2360471 A1    8/2011
(Continued)

OTHER PUBLICATIONS

Chen et al.,"Detection of Total and A1c-Glycosylated Hemoglobin in Human Whole Blood Using Sandwich Immunoassays on Polydimethylsiloxane-Based Antibody Microarrays"Anal. Chem. 2012, 84, 8635-8641 (Year: 2012).*

(Continued)

*Primary Examiner* — Dennis White
(74) *Attorney, Agent, or Firm* — Duane Morris LLP

(57) ABSTRACT

A sensor according to a first embodiment of the present invention includes a flow channel to permit passage of a specimen, a first detection part that is located in the flow channel and has a first ligand specifically bindable to a first material in the specimen, and a second detection part that is located downstream of the first detection part in the flow channel and has a second ligand specifically bindable to the first material and/or a second material in the specimen.

19 Claims, 9 Drawing Sheets

(51) Int. Cl.
*G01N 33/543* (2006.01)
*G01N 33/558* (2006.01)
*G01N 33/487* (2006.01)
*B01L 3/00* (2006.01)

(52) U.S. Cl.
CPC ....... *C12Q 1/001* (2013.01); *G01N 33/48785* (2013.01); *G01N 33/5438* (2013.01); *G01N 33/558* (2013.01); *G01N 33/723* (2013.01); *B01L 2300/0636* (2013.01); *B01L 2300/0663* (2013.01); *B01L 2300/0809* (2013.01); *B01L 2300/0816* (2013.01); *B01L 2300/0861* (2013.01); *B01L 2300/0874* (2013.01); *B01L 2300/0887* (2013.01); *B01L 2400/0406* (2013.01); *B01L 2400/0436* (2013.01); *G01N 2333/805* (2013.01)

(58) Field of Classification Search
CPC ......... G01N 2333/805; B01L 3/502715; B01L 3/502; B01L 2300/0887; B01L 2300/0874; B01L 2400/0436; B01L 2300/0816; B01L 2300/0636; B01L 2400/0406; B01L 2300/0663; B01L 2300/0809; B01L 2300/0861; C12Q 1/001
See application file for complete search history.

(56) References Cited

U.S. PATENT DOCUMENTS

| | | | |
|---|---|---|---|
| 2004/0191124 A1* | 9/2004 | Noetzel | B01L 3/502746 422/69 |
| 2005/0037484 A1* | 2/2005 | Staimer | B01L 3/502707 435/287.2 |
| 2009/0320574 A1* | 12/2009 | Yamada | G01N 29/022 73/64.53 |
| 2010/0055716 A1 | 3/2010 | Tsutsui et al. | |
| 2011/0117670 A1 | 5/2011 | Walker et al. | |
| 2011/0318765 A1 | 12/2011 | Miyazaki et al. | |
| 2014/0073532 A1 | 3/2014 | Walker et al. | |
| 2014/0224002 A1 | 8/2014 | Fukuura et al. | |
| 2016/0068594 A1 | 3/2016 | Walker et al. | |
| 2016/0327575 A1 | 11/2016 | Tanaka et al. | |

FOREIGN PATENT DOCUMENTS

| | | |
|---|---|---|
| JP | H09196920 A | 7/1997 |
| JP | H11133027 A | 5/1999 |
| JP | 2000-065839 A | 3/2000 |
| JP | 2002-303629 A | 10/2002 |
| JP | 2002-365290 A | 12/2002 |
| JP | 2007-003410 A | 1/2007 |
| JP | 2007-003411 A | 1/2007 |
| JP | 2008-292211 A | 12/2008 |
| JP | 2010-054308 A | 3/2010 |
| JP | 2012251789 A | 12/2012 |
| JP | 2013-511717 A | 4/2013 |
| JP | 6284552 B2 | 2/2018 |
| WO | WO 2010/067612 A1 | 6/2010 |
| WO | WO 2011/062803 A2 | 5/2011 |
| WO | 2013/015443 A1 | 1/2013 |

OTHER PUBLICATIONS

International Search Report in International Application No. PCT/JP2014/084515, dated Apr. 7, 20015, in 2 pages.

Official Action dated Jul. 25, 2017, in corresponding Japanese Patent Application No. 2015-555043 with Statement of Relevance of Non-English References.

* cited by examiner

Fig. 1
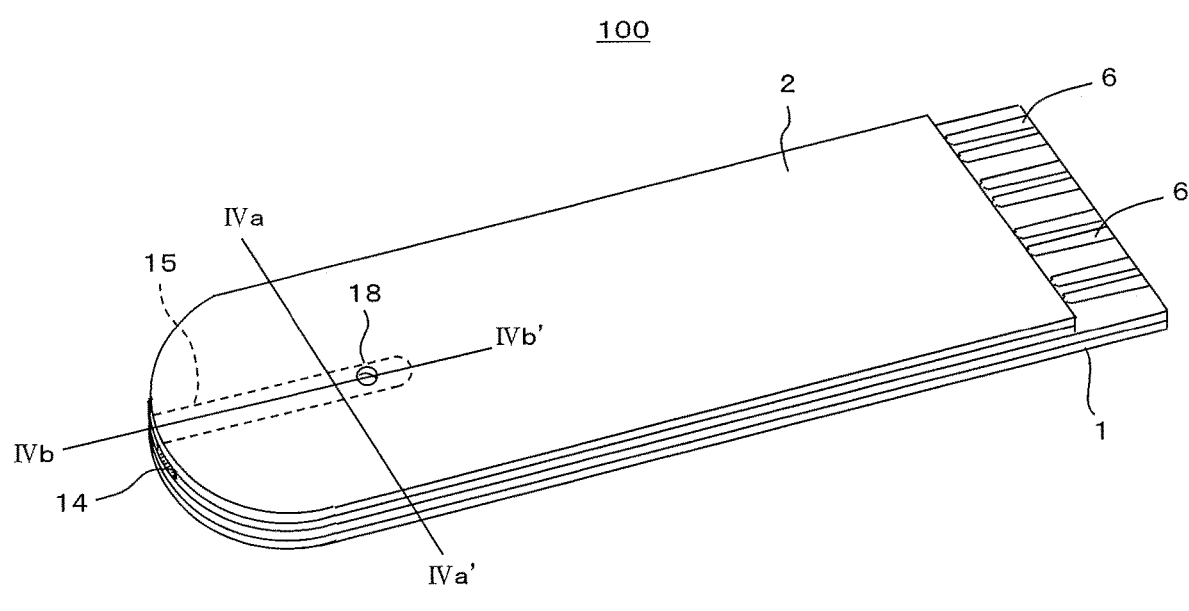
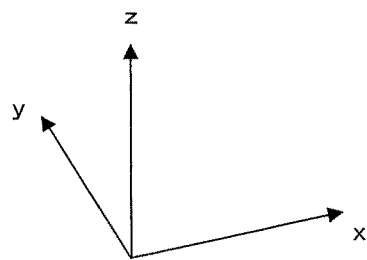

ially bindable to the first material while maintaining the
SENSOR

TECHNICAL FIELD

The present invention relates to a sensor capable of measuring nature or ingredients of a specimen.

BACKGROUND ART

An analytical tool to measure nature or ingredients of a specimen has been known (for example, refer to Japanese Unexamined Patent Publication No. 11-133027).

SUMMARY OF THE INVENTION

The technology described in Japanese Unexamined Patent Publication No. 11-133027 is, however, the analytical tool using light. An Hb measurement part to measure Hb (hemoglobin) is disposed on an upstream side thereof, and HbA1c is to be detected in a state of being bound to a reagent in a reagent mounting part disposed on a downstream side of the Hb measurement part, at an analysis part located on a more downstream side.

Therefore, the configuration of a sensor is complicated, and various kinds of reactions need to be sequentially and accurately carried out in a process in which the specimen flows through a flow channel, thus making it difficult to obtain sufficient detection accuracy.

Hence, there has been a desire for a sensor capable of accurately measuring a detection object contained in the specimen with a simple configuration.

A sensor according to a first embodiment of the present invention includes a flow channel to permit passage of a specimen, a first detection part that is located in the flow channel and has a first ligand specifically bindable to a first material in the specimen, and a second detection part that is located downstream of the first detection part in the flow channel and has a second ligand specifically bindable to the first material and a second material in the specimen.

A sensor according to a second embodiment of the present invention includes a flow channel to permit passage of a specimen, a first detection part that is located in the flow channel and has a first ligand specifically bindable to a first material in the specimen, and a second detection part that is located downstream of the first detection part in the flow channel and has a second ligand specifically bindable to a second material in the specimen. A concentration of the first material is smaller than a concentration of the second material in the specimen.

With the sensors of the present embodiments, the first material and the second material are accurately detectable with a relatively simple configuration that includes the first detection part having the first ligand specifically bindable to the first material, and the second detection part having the second ligand specifically bindable to the second material. Additionally, the first detection part is located upstream of the second detection part. Hence, the specimen firstly passes through the first detection part having the first ligand specifically bindable to the first material while maintaining the concentration of the first material and the concentration of the second material, and thereafter passes through the second detection part. This makes it possible to improve detection accuracy for the first material.

BRIEF DESCRIPTION OF THE DRAWINGS

FIG. 1 is a perspective view of a sensor according to a first embodiment of the present invention;

FIG. 4 is a diagram showing the sensor shown in FIG. 1, specifically, a sectional view showing in enlarged dimension a state in which the sensor is cut along each line in FIG. 1, that is.

EMBODIMENTS FOR CARRYING OUT THE INVENTION

Figure 2:
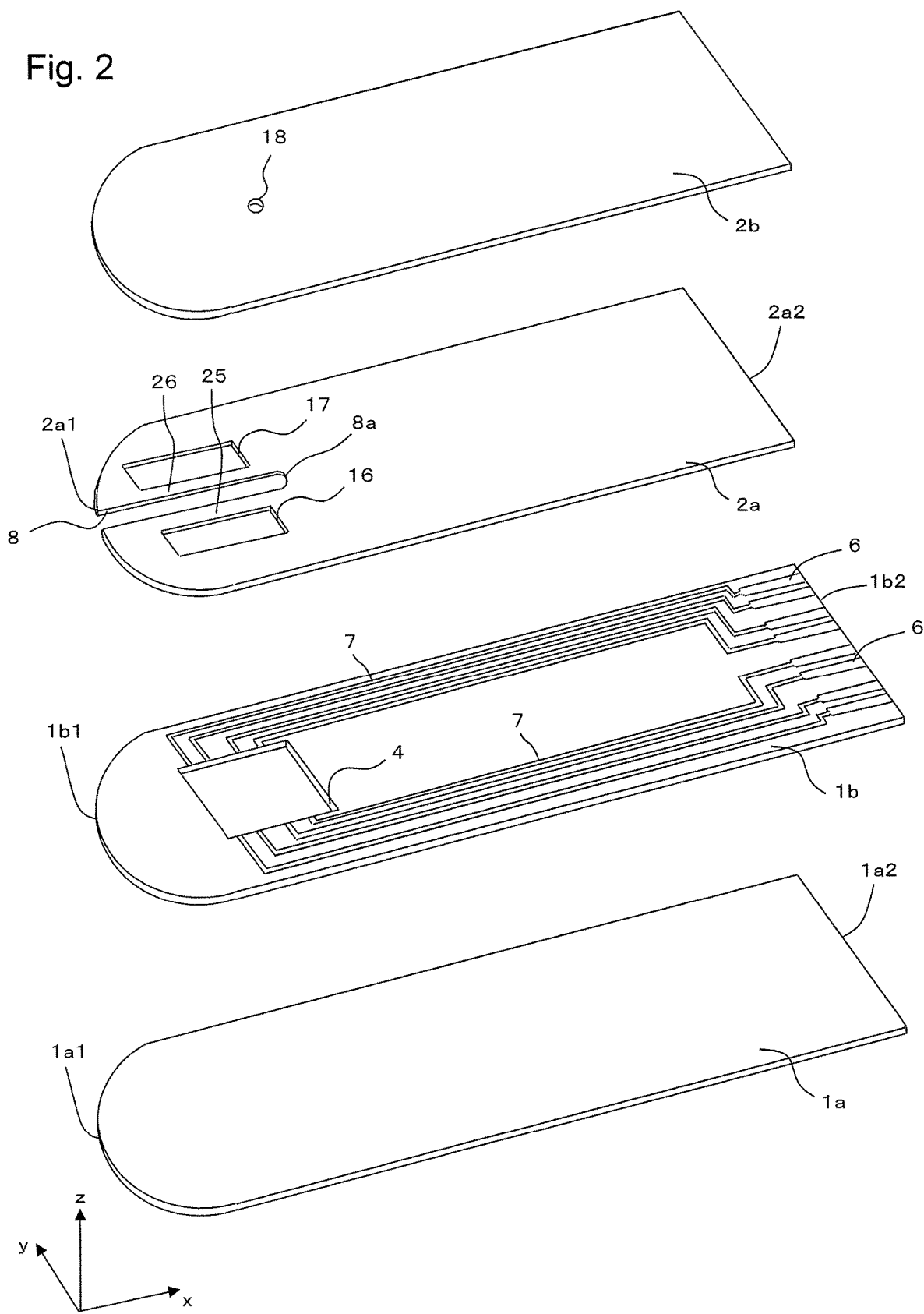
FIG. 2 is an exploded perspective view of a first cover member and a second cover member of the sensor shown in FIG. 1.

Sensors respectively according to embodiments of the present invention are described in detail below by exemplifying a case where a specimen is in a liquid state (specimen liquid) while appropriately referring to the drawings.

<Sensor of First Embodiment>

The sensor according to the first embodiment of the present invention includes a flow channel to permit passage of the specimen liquid, a first detection part having a first ligand that is located in the flow channel and has a first ligand capable of specific binding to a first material in the specimen liquid, and a second detection part that is located downstream of the first detection part in the flow channel and has a second ligand capable of specific binding to the first material and a second material in the specimen liquid.

The sensor of the present embodiment is applicable to a detection method of detecting a state change on a surface of a base body. A structure of the sensor of the present embodiment is described in detail below by exemplifying an SAW sensor using an SAW (Surface Acoustic Wave). The SAW sensor is preferable from a viewpoint of achieving downsizing.

The sensor 100 is mainly made up of a first cover member 1, a second cover member 2, and a detection element 3. The sensor 100 has a first cover member configured to dispose a base body on an upper surface thereof, and a second cover member connected to the first cover member. The sensor 100 further has an inlet that permits entrance of the specimen liquid, and is disposed on at least one of the first cover member and the second cover member, and a groove part (flow channel) extending from the inlet to at least above the upper surface (surface) of the base body. As an example of the present embodiment, for example, in the sensor 100 as the SAW sensor, the first cover member has a recess on an upper surface thereof and the base body is accommodated in the recess, and the second cover member has the groove part. The sensor 100 has a first IDT (Inter Digital Transducer) electrode, which is located on the upper surface of the base body, and generates an acoustic wave that propagates toward a detection part 13a described later. The sensor 100 also has a second IDT electrode, which is located on the upper surface of the base body and receives an acoustic wave after passing through the detection part 13a. The sensor 100 further has a first connection member which is connected to the upper surface of the base body on the first IDT electrode with a first vibration space interposed therebetween, and which tightly closes the first IDT electrode in the first vibration space. The sensor 100 also has a second connection member which is connected to the upper surface of the base body on the second IDT electrode with a second vibration space interposed therebetween, and which tightly closes the second IDT electrode in the second vibration space. That is, the sensor 100 has the first connection member that is connected to the upper surface of the base body and has the closed first vibration space between the first connection member and the upper surface of the base body. The sensor 100 also has the second connection member that is connected to the upper surface of the base body and has the closed second vibration space between the second connection member and the upper surface of the base body. In the sensor 100, the first vibration space is located on the first IDT electrode, and the second vibration space is located on the second IDT electrode.

An exemplified configuration of the sensor 100 is described in detail below while appropriately referring to the drawings. Similar reference numerals are used to denote similar structural members in the drawings in the following description. For example, sizes of individual structural members and a distance between the members are schematically illustrated, and may be different from those of actual products thereof. Either direction in the sensor 100 may be an upward or downward direction. However, in the following, an xyz orthogonal coordinate system is defined, a positive side in z-direction is taken as the upward direction, and terms, such as an upper surface and a lower surface, are used for the sake of convenience.

Individual components of the sensor 100 are described in detail below.

(Cover Member)

As shown in FIGS. 1 and 2, the first cover member 1 has a first base body 1a and a second base body 1b laminated on the first base body 1a. The second cover member 2 has a third base body 2a laminated on the second base body 1b, and a fourth base body 2b laminated on the third base body 2a.

The first cover member 1 and the second cover member 2 are stuck together, and the detection element 3 is accommodated inside the first cover member 1 and the second cover member 2 being stuck together. The first cover member 1 has a recess 5 on the upper surface thereof, and the detection element 3 is disposed in the recess 5 as shown in the sectional view of FIG. 4.

As shown in FIG. 1, the second cover member 2 has an inlet 14, which is an inlet for a specimen liquid, at an end in a longitudinal direction (x direction), and a groove part 15 extending from the inlet 14 toward a portion immediately above the detection element 3. In FIG. 1, the groove part 15 is indicated by a broken line in order to show a position of the groove part 15. The groove part 15 functions as a flow channel in the present embodiment. Therefore, a flow channel described later is described using the same reference numeral as the groove part.

(First Cover Member)

As shown in FIG. 2, the first base body 1a constituting the first cover member 1 has a tabular form and a thickness of, for example, 0.1-0.5 mm. A planar shape of the first base body 1a is an approximately rectangular shape, and one end 1a1 thereof in the longitudinal direction has a circular arc shape protruding outward. An external form of the one end 1a1 in a plan view may be a curvilinear form protruding outward. This is also true for the second base body 1b, the third base body 2a, and the fourth base body 2b.

A length of the base body in the x direction is, for example, 1-5 cm, and a length thereof in y direction is, for example, 1-3 cm. Hereinafter, when a numerical range is indicated using "-", the numeral range includes a lower limit value and an upper limit value unless otherwise noted. For example, a numeral range "0.1-0.5 mm" indicates that a lower limit is "0.1 mm or more" and an upper limit is "0.5 mm or less" unless otherwise noted.

The second base body 1b is stuck to an upper surface of the first base body 1a. The second base body 1b is made into a tabular frame in which a through hole 4 for forming a recess is disposed on a tabular plate. A thickness of the second base body 1b is, for example, 0.1-0.5 mm. An external form of the second base body 1b in the plan view is approximately the same as that of the first base body 1a, and a length thereof in the x direction and a length thereof in the y direction are also approximately the same as those of the first base body 1a.

The through hole 4 for forming the recess is located close to the one end 1b1 of the second base body 1b, and penetrates the second base body 1b in a thickness direction. The recess 5 is to be formed in the first cover member 1 by connecting the second base body 1b with the through hole 4 for forming the recess to the tabular first base body 1a (refer to FIG. 4). That is, the upper surface of the first base body 1a located inside the through hole 4 for forming the recess becomes a bottom surface of the recess 5, and an inner wall of the through hole 4 for forming the recess becomes an inner wall of the recess 5. In other words, the upper surface of the first base body 1a exposed from the through hole 4 for forming the recess becomes the bottom surface of the recess 5, and the inner wall of the through hole 4 for forming the recess becomes the inner wall of the recess 5.

A terminal 6 and a wiring line 7 being laid from the terminal 6 to the through hole 4 for forming the recess are disposed on an upper surface of the second base body 1b. The terminal 6 is disposed at another end 1b2 in the x direction on the upper surface of the second base body 1b. A portion provided with the terminal 6 corresponds to a portion that permits insertion of an external measuring device (not shown) when the sensor 100 is actually inserted into the external measuring device, and the sensor 100 is to be electrically connected to the external measuring device via the terminal 6. The terminal 6 and the detection element 3 are electrically connected to each other via the wiring line 7 or the like. A signal from the external measuring device is to be inputted via the terminal 6 to the sensor 100, and a signal from the sensor 100 is to be outputted via the terminal 6 to the external measuring device.

(Second Cover Member)

The second cover member 2 is connected to the upper surface of the first cover member 1 made up of the first base body 1a and the second base body 1b. The second cover member 2 has the third base body 2a and the fourth base body 2b.

The third base body 2a is stuck to an upper surface of the second base body 1b. The third base body 2a has a tabular form and a thickness of, for example, 0.1-0.5 mm. A planar shape of the third base body 2a is an approximately rectangular shape. Similarly to the first base body 1a and the second base body 1b, one end 2a1 in the longitudinal direction has a circular arc shape protruding outward. A length of the third base body 2a in the x direction is made slightly shorter than the length of the second base body 1b in the x direction so that the terminal 6 disposed on the second base body 1*b* is exposed when the third base body 2*a* is stuck to the upper surface of the second base body 1*b* (refer to FIG. 1). A length of the third base body 2*a* in the x direction is, for example, 0.8 mm-4.8 cm. A length thereof in the y direction is, for example, 1-3 cm as in the first base body 1*a* and the second base body 1*b*.

A notch 8 is formed on the third base body 2*a*. The notch 8 is obtainable by notching the third base body 2*a* from a top portion of the circular arc-shaped one end 2*a*1 to the another end 2*a*2 in the x direction on the third base body 2*a*. The notch 8 is for forming the groove part 15. A first through hole 16 and a second through hole 17 that penetrate the third base body 2*a* in the thickness direction are disposed on both adjacent sides of the notch 8 of the third base body 2*a*. When the third base body 2*a* is laminated on the second base body 1*b*, a connection part between the detection element 3 and the wiring line 7 is to be located inside the first through hole 16 and the second through hole 17. As described later, a part of the third base body 2*a* which is located between the first through hole 16 and the notch 8 becomes a first partition part 25 that partitions the groove part 15 and a space formed by the first through hole 16, and a part of the third base body 2*a* which is located between the second through hole 17 and the notch 8 becomes a second partition part 26 that partitions the groove part 15 and a space formed by the second through hole 17.

The fourth base body 2*b* is stuck to an upper surface of the third base body 2*a*. The fourth base body 2*b* has a tabular form and a thickness of, for example, 0.1-0.5 mm. An external form of the fourth base body 2*b* in the plan view is approximately the same as that of the third base body 2*a*, and a length thereof in the x direction and a length thereof in the y direction are also approximately the same as those of the third base body 2*a*. The groove part 15 is to be formed on a lower surface of the second cover member 2 by connecting the fourth base body 2*b* to the third base body 2*a* provided with the notch 8. That is, a lower surface of the fourth base body 2*b* located inside the notch 8 becomes a bottom surface of the groove part 15, and an inner wall of the notch 8 becomes an inner wall of the groove part 15. In other words, the lower surface of the fourth base body 2*b* being exposed from the notch 8 becomes the bottom surface of the groove part 15, and the inner wall of the notch 8 becomes the inner wall of the groove part 15. The groove part 15 extends from the inlet 14 to at least a region immediately above the detection part 13*a*, and has, for example, a rectangular cross-sectional shape.

A third through hole 18 that penetrates the fourth base body 2*b* in the thickness direction is formed in the fourth base body 2*b*. The third through hole 18 is located on an end portion 8*a* of the notch 8 when the fourth base body 2*b* is laminated on the third base body 2*a*. Accordingly, an end portion of the groove part 15 is connected to the third through hole 18. The third through hole 18 is for releasing, for example, air in the groove part 15 to the outside.

The first base body 1*a*, the second base body 1*b*, the third base body 2*a*, and the fourth base body 2*b* are made of paper, plastic, celluloid, ceramics, or the like. All of these base bodies are formable with the same material. By forming these base bodies with the same material, all of these base bodies are capable of having approximately the same coefficient of thermal expansion, thereby reducing deformation due to a difference in coefficient of thermal expansion among these base bodies. Biomaterials can be applied to the detection part 13*a*, and some of them are liable to deteriorate due to external light, such as ultraviolet rays. On that occasion, it is necessary to use an opaque material having light-shielding properties as a material of the first cover member 1 and the second cover member 2. When the detection part 13*a* is subject to little or no deterioration due to the external light, the second cover member 2 provided with the groove part 15 may be formed using a nearly transparent material. This permits visual observation of a situation of the specimen liquid flowing through the flowing channel 15.

(Detection Element)

The detection element 3 is described below.

Figure 5:
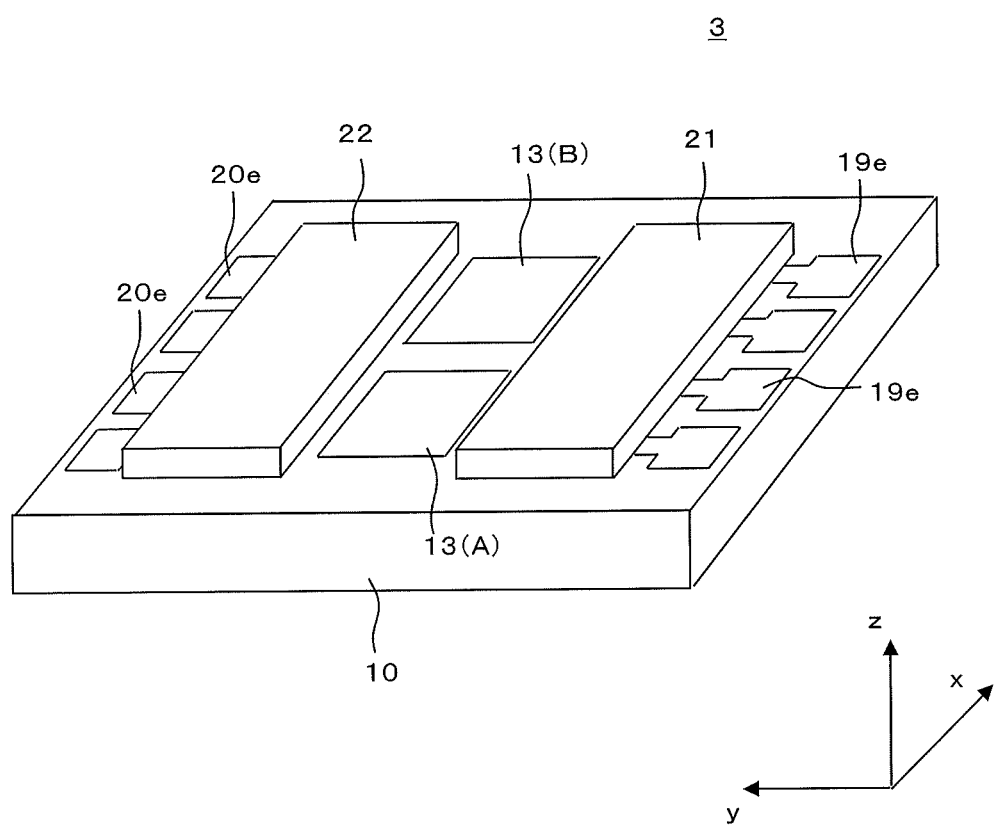
FIG. 5 is a perspective view of a detection element for use in the sensor shown in FIG. 1.
Figure 6:
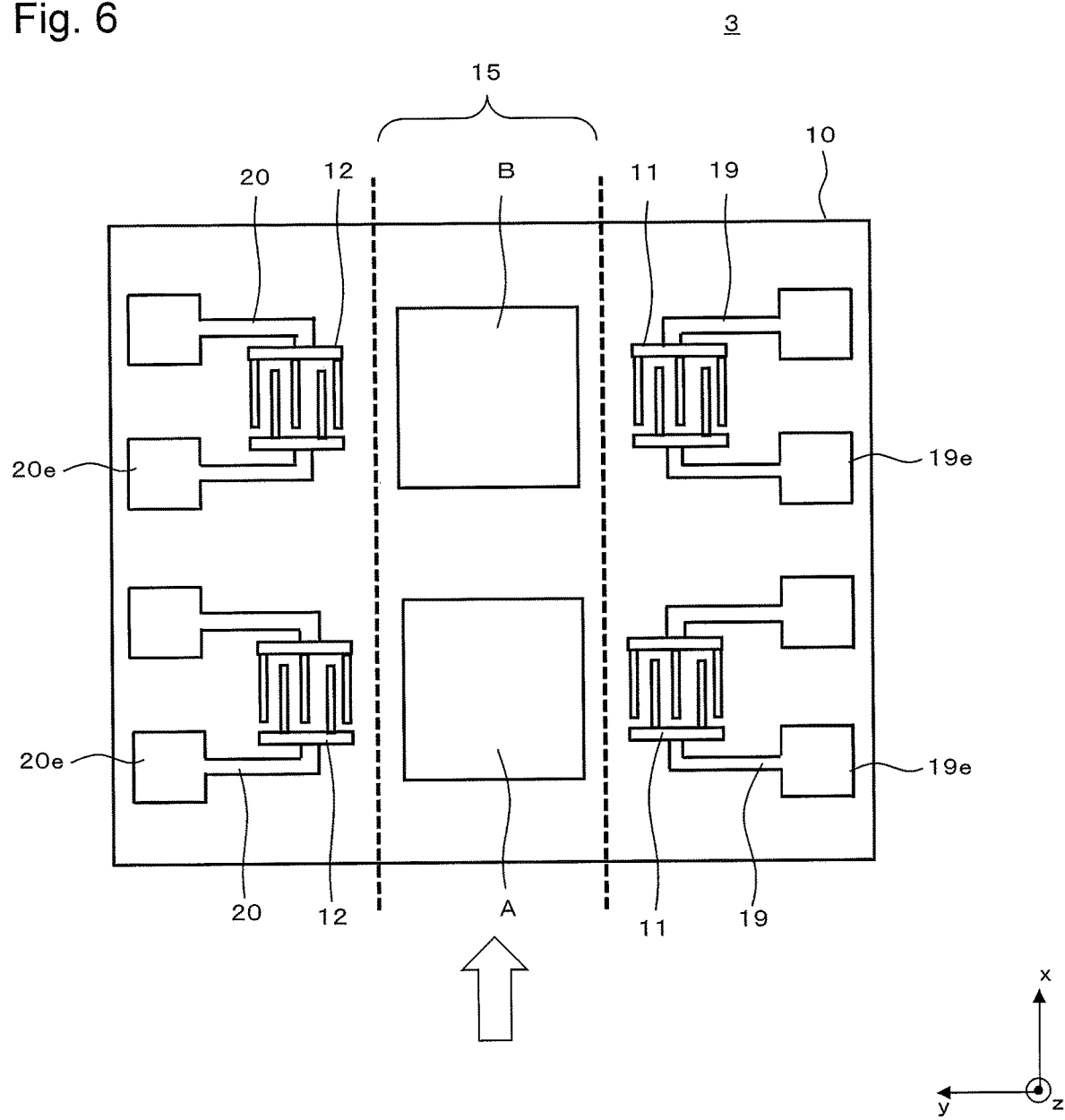
FIG. 6 is a plan view of a state in which a first connection member and a second connection member of the detection element shown in FIG. 5 are removed.

As shown in FIGS. 5 and 6, the detection element 3 is the surface acoustic wave element as described above, and mainly has a base body 10, a first IDT electrode 11, a second IDT electrode 12, and a detection part 13*a*, each of which is located on an upper surface of the base body 10. The detection element 3 further has a first extraction electrode 19 and a second extraction electrode 20.

(Base Body)

The base body 10 is composed of a single crystal having piezoelectricity, such as lithium tantalate ($LiTaO_3$) single crystal, lithium niobate ($LiNbO_3$) single crystal, or quartz. A planar shape and dimensions of the base body 10 are appropriately settable. For example, a thickness of the base body 10 is 0.3-1.0 mm.

(IDT Electrodes and Extraction Electrodes)

The first IDT electrode 11 has a pair of interdigital electrodes as shown in FIG. 6. Each of the interdigital electrodes has two bus bars facing each other and a plurality of electrode fingers extending from each of the bus bars to another one. The pair of interdigital electrodes is disposed so that the electrode fingers mesh with each other. The second IDT electrode 12 is configured similarly to the first IDT electrode 11. The first IDT electrode 11 and the second IDT electrode 12 constitute a transversal type IDT electrode.

Here, it is possible to design frequency characteristics by using, as a parameter, the number of the electrode fingers between the first IDT electrode 11 and the second IDT electrode 12, a distance between the electrode fingers adjacent to each other, and a crossing width of the electrode fingers. Examples of SAWS to be excited by the IDT electrodes include Rayleigh wave, Love wave, and Leaky wave. An elastic member for reducing reflection of the SAW may be disposed at an outer region of each of the first IDT electrode 11 and the second IDT electrode 12 in a propagation direction of the SAW (the y direction). A frequency of the SAW is settable in a range of, for example, several megahertz (MHz) to several gigahertz (GHz). Particularly, a range from several hundreds MHz to 2 GHz is practical and makes it possible to achieve downsizing of the base body 10 as well as downsizing of the SAW sensor.

The first IDT electrode 11 is for generating a predetermined surface acoustic wave (SAW), and the second IDT electrode 12 is for receiving the SAW generated by the first IDT electrode 11. The first IDT electrode 11 and the second IDT electrode 12 are disposed on the same straight line so that the second IDT electrode 12 can receive the SAW generated by the first IDT electrode 11. As described above, it is possible to design the frequency characteristics by using, as a parameter, the number of the electrode fingers between the first IDT electrode 11 and the second IDT electrode 12, the distance between the electrode fingers adjacent to each other, and the crossing width of the electrode fingers. As an SAW excited by the IDT electrode, there are ones having different vibrational modes. The detection element 3 employs, for example, a vibrational mode of a transverse wave that is called SH wave.

The first IDT electrode 11 is connected to the first extraction electrode 19. The first extraction electrode 19 is extracted from the first IDT electrode 11 toward the side opposite the detection part 13a, and an end portion 19e of the first extraction electrode 19 is electrically connected to the wiring line 7 disposed on the first cover member 1. The second IDT electrode 12 is connected to the second extraction electrode 20. The second extraction electrode 20 is extracted from the second IDT electrode 12 toward the side opposite the detection part 13a, and an end portion 20e of the second extraction electrode 20 is electrically connected to the wiring line 7.

The first IDT electrode 11, the second IDT electrode 12, the first extraction electrode 19, and the second extraction electrode 20 are made of, for example, aluminum or an alloy of aluminum and copper (aluminum alloy). These electrodes may have a multilayer structure. When employing the multilayer structure, for example, a first layer is made of titanium or chrome, and a second layer is made of aluminum or the aluminum alloy.

The first IDT electrode 11 and the second IDT electrode 12 are respectively covered with a protection film (not shown). The protection film contributes to reducing oxidation of the first IDT electrode 11 and the second IDT electrode. The protection film is made of, for example, silicon oxide, aluminum oxide, zinc oxide, titanium oxide, silicon nitride, or silicon. A thickness of the protection film is, for example, approximately 1/10 of a thickness of each of the first IDT electrode 11 and the second IDT electrode 12 (namely, 10-30 nm). The protection film may be formed over the entire upper surface of the base body 10 so as to expose the end portion 19e of the first extraction electrode 19 and the end portion 20e of the second extraction electrode 20.

(Connection Members and Vibration Spaces)

Figure 4A:
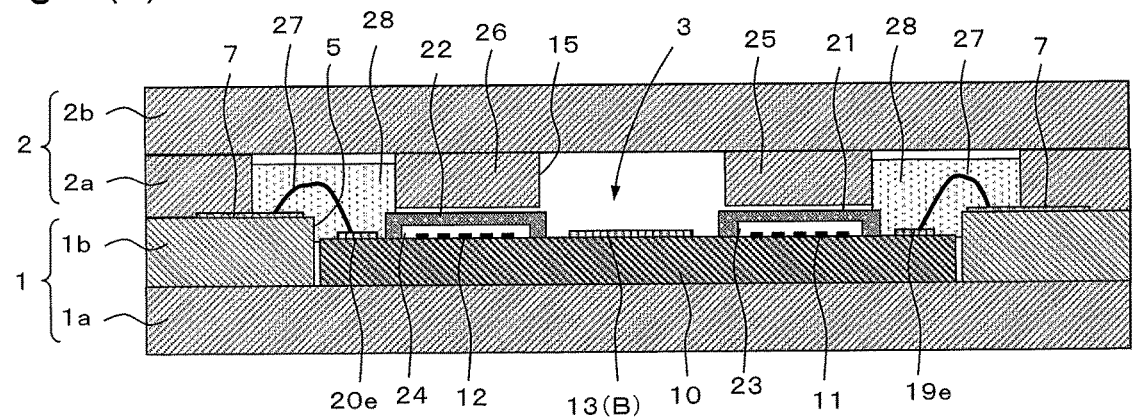
FIG. 4(a) is a sectional view cut along a line IVa-IVa'.

The first IDT electrode 11 may be covered with the first connection member 21 as shown in FIG. 5. The first connection member 21 is located on the upper surface of the base body 10, and an interior thereof is hollow. A hollow part of the first connection member 21 in a state in which the first connection member 21 is mounted on the upper surface of the base body 10 corresponds to a first vibration space 23 (refer to FIG. 4(a)). The first IDT electrode 11 is sealed within the first vibration space 23. The first IDT electrode 11 is therefore kept away from outside air and the specimen liquid, thereby protecting the first IDT electrode 11. Ensuring the first vibration space 23 makes it possible to reduce deterioration of the characteristics of the SAW to be excited by the first IDT electrode 11. Similarly, the second IDT electrode 12 may be covered with the second connection member 22. Similarly to the first connection member 21, the second connection member 22 is also located on the upper surface of the base body 10, and an interior thereof is hollow as shown in FIG. 4(a). A hollow part of the second connection member 22 in a state in which the second connection member 22 is mounted on the upper surface of the base body 10 corresponds to the second vibration space 24. The second IDT electrode 12 is sealed within the second vibration space 24.

The vibration space may have an optional shape according to the shape and arrangement of the IDT electrodes, for example, a parallelopiped shape, a dome shape in a sectional view, or an elliptical shape in the plan view.

The first connection member 21 is made up of a circular arch-shaped frame body fixed to the upper surface of the base body 10 so as to surround two first IDT electrodes 11 disposed along the x direction, and a lid body fixed to the frame body so as to close an opening of the frame body. This structure is formable, for example, by forming a resin film using a photosensitive resin material, and then patterning the resin film by a photolithography method or the like. The second connection member 22 is similarly formable.

Although the two first IDT electrodes 11 are covered with the single first connection member 21 in the sensor 100, the two first IDT electrodes 11 may be individually covered with the first connection member 21. Alternatively, the two first IDT electrodes 11 may be covered with the single first connection member 21, and a partition may be disposed between the two first IDT electrodes 11. This is also true for the second IDT electrode 12. That is, the two second IDT electrodes 12 may be individually covered with the second connection member 22. Alternatively, the single second connection member 22 may be used and a partition may be disposed between the two second IDT electrodes 12.

(Detection Part and Reference Part)

The detection part 13a (and a reference part 13b) is disposed between the first IDT electrode 11 and the second IDT electrode 12 as shown in FIGS. 3 to 9. The detection part 13a and the reference part 13b are indicated in FIGS. 3 to 9 as follows. That is, in FIGS. 3 to 5, the first detection part D1 is indicated by reference numerals 13(A), and the second detection part D2 is indicated by reference numeral 13(B). In FIGS. 6 to 9, the detection part 13a and the reference part 13b are indicated by reference characters A to F in order from the upstream side for the sake of convenience without distinguishing between the detection part 13a and the reference part 13b. In FIG. 6, the first detection part D1 is indicated by reference character A, and the second detection part D2 is indicated by reference character B.

In the sensor 100 of the present embodiment, as shown in FIGS. 3 to 6, the detection part 13a has the first detection part D1 (13(A)) and the second detection part D2 (13(B)) (configuration example 1). There needs to be at least one first detection part D1. This is also true for the second detection part D2. That is, there needs to be at least one second detection part D2. The present embodiment employs the single first detection part D1 and the single second detection part D2.

Here, the first detection part D1 is located in the flow channel 15, and has the first ligand LG1 (not shown) capable of specific binding to the first material in the specimen liquid. The second detection part D2 is located downstream of the first detection part D1 in the flow channel 15, and has the second ligand LG2 (not shown) capable of specific binding to the first material and the second material in the specimen liquid. The concept of "upstream" and "downstream" means a relative positional relationship in the flow channel 15, and the "downstream" means a location in a flow direction of the specimen in the flow channel 15, through which the specimen passes later. For example, in FIG. 4(b), the 13(B) that is the second detection part D2 is located downstream of the 13(A) that is the first detection part D1. When the first material is HbA1c, an anti-HbA1c antibody needs to be used as the first ligand LG1. When the second material is at least one kind of Hb, an anti-Hb antibody needs to be used as the second ligand LG2. The second material may contain the first material.

The detection part 13a has, for example, a metal film, PEG (polyethylene glycol) immobilized to a surface of the metal film, and a ligand. The ligand is one which is capable of specific binding to a specific target material, such as an antibody or an aptamer composed of nucleic acid and peptide. The metal film has a two-layer structure made up of, for example, chrome, and gold being deposited on the chrome.

That is, the detection part 13a is for causing a reaction with a target material as a detection object material contained in the specimen liquid. Specifically, when the specimen liquid comes into contact with the detection part 13a, a specific target material in the specimen liquid binds to the antibody or aptamer that is the ligand corresponding to the target material. For example, as described above, the first ligand LG1 of the first detection part D1 specifically binds to HbA1c as the first material, and the second ligand LG2 of the second detection part D2 specifically binds to Hb as the second material. When the first IDT electrode 11, the second IDT electrode 12, and the detection part 13a, which are disposed along the y direction as shown in FIGS. 5 and 6, are taken here as one set, two sets thereof are disposed in the sensor 100. This makes it possible for the single sensor to detect two kinds of materials by ensuring that the target material (first material) to be reacted at the first detection part D1 is different from the target material (second material) to be reacted at the second detection part D2.

Thus, with the sensor 100 of the present embodiment, the first material and the second material are accurately detectable with a relatively simple configuration that includes the first detection part D1 having the first ligand capable of specific binding to the first material, and the second detection part D2 having the second ligand capable of specific binding to the second material. Additionally, because the first detection part D1 is located upstream of the second detection part D2, the specimen liquid firstly passes through the first detection part D1 having the first ligand capable of specific binding to the first material, while maintaining a concentration of the first material and a concentration of the second material, and thereafter passes through the second detection part D2. This makes it possible to improve detection accuracy for the first material. Furthermore, the detection element is downsizable because the detection part 13a can be configured by the first detection part D1 and the second detection part D2.

(Measurement by Measuring Device)

When a detection of a specimen is carried out in the detection element 3 using an SAW, firstly, a predetermined voltage is applied from the external measuring device to the first IDT electrode 11 through the wiring line 7 and the first extraction electrode 19. That is, a sensor device is obtainable by adding the measuring device to the sensor 100 according to the foregoing embodiment.

When the voltage is so applied, the upper surface of the base body 10 is excited in a formation region of the first IDT electrode 11, and an SAW having a predetermined frequency is generated. Part of the generated SAW propagates toward the detection part 13a, and passes through the detection part 13a and then reaches the second IDT electrode 12. Here, at the detection part 13a, the aptamer of the detection part 13a binds to the specific target material in the specimen liquid, a weight of the detection part 13a changes according to a quantity of binding. Consequently, a change occurs in characteristics, such as a phase of the SAW passing under the detection part 13a. When the SAW whose characteristic has been changed reaches the second IDT electrode 12, a voltage according thereto is to be generated in the second IDT electrode 12.

The voltage is then outputted to the outside through the second extraction electrode 20 and the wiring line 7, and the nature and ingredients of the specimen can be examined by reading the voltage with the external measuring device.

(Flow Channel)

The sensor 100 of the present embodiment uses capillary action in order to introduce the specimen liquid into the detection part 13a.

Figure 4B:
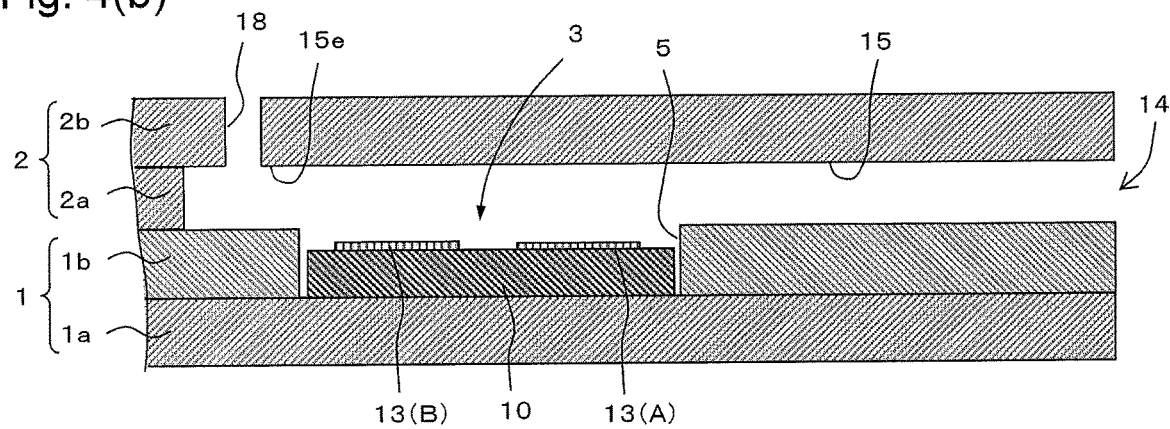
FIG. 4(b) is a sectional view cut along a line IVb-IVb'.

To be specific, a part of the groove part 15, which is formed on the lower surface of the second cover member 2 by connection of the second cover member 2 to the first cover member 1, becomes an elongated tube. It is therefore possible to cause the elongated tube formed by the groove part 15 to generate capillary action by setting a width or diameter of the groove part 15 to a predetermined value in consideration of the kind of the specimen liquid and the material of each of the first cover member 1 and the second cover member 2. A width (a dimension in the y direction) of the groove part 15 is, for example, 0.5-3 mm, and a depth thereof (a dimension in the z direction) is, for example, 0.1-0.5 mm. As shown in FIG. 4(b), the groove part 15 has an extension portion 15e that is a portion extending beyond the detection part 13a, and the third through hole 18 being connected to the extension portion 15e is formed in the second cover member 2. Upon entrance of the specimen liquid into the flow channel 15, air that is already present in the flow channel 15 is to be released from the third through hole 18 to the outside.

By forming the tube that generates capillary action in the cover member made up of the first cover member 1 and the second cover member 2, upon contact of the specimen liquid with the inlet 14, the specimen liquid is to be sucked into the cover member by using the groove part 15 as the flow channel 15. Thus, the sensor 100 includes therein a suction mechanism for the specimen liquid, and is therefore capable of sucking the specimen liquid without using any tool, such as a pipette. A region including the inlet 14 is rounded, and the inlet 14 is disposed at a top portion of the region, thus making it easier to distinguish the inlet 14.

Meanwhile in the present embodiment, the flow channel 15 for the specimen liquid formed by the groove part 15 has a depth of approximately 0.3 mm, and the detection element 3 has a thickness of approximately 0.3 mm. That is, the depth of the flow channel 15 and the thickness of the detection element 3 are approximately equal. Therefore, the flow channel 15 may be closed when the detection element 3 is directly disposed on the surface of the flow channel 15. Hence, in the sensor 100, the flow channel 15 for the specimen liquid is configured so as not to be closed by disposing the recess 5 on the first cover member 1 configured to mount the detection element 3 thereon, and accommodating the detection element 3 in the recess 5 as shown in FIG. 4. That is, the flow channel 15 formed by the groove part 15 is ensured by setting the depth of the recess 5 and the thickness of the detection element 3 to approximately the same degree, and then mounting the detection element 3 into the recess 5.

Figure 3:
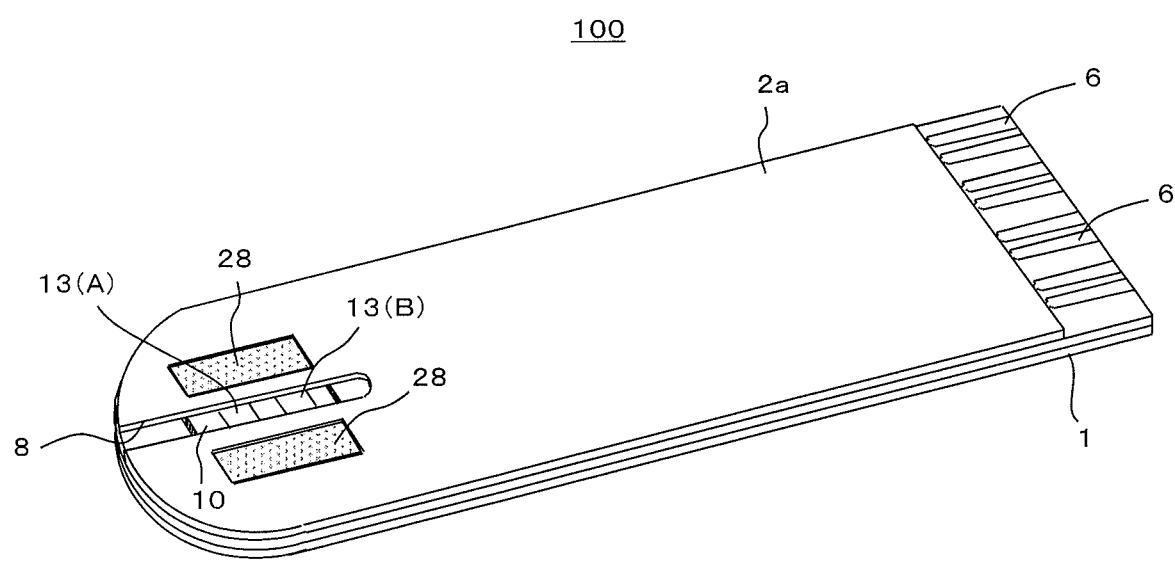
FIG. 3 is a perspective view in a state in which a fourth base body of the sensor shown in FIG. 1 is removed.

FIG. 3 is a perspective view in a state in which the fourth base body 2b of the second cover member 2 is removed. The flow channel 15 (notch 8) for the specimen liquid is so ensured, and it is therefore possible to smoothly introduce the specimen liquid that has entered the flow channel 15 into the detection part 13a.

From the viewpoint of sufficiently ensuring the flow channel 15 for the specimen liquid, a height of the upper surface of the base body 10 from the bottom surface of the recess 5 needs to be identical to or smaller than the depth of the recess 5 as shown in FIG. 4. For example, by setting the height of the upper surface of the base body 10 from the bottom surface of the recess 5 to be equal to the depth of the recess 5, the bottom surface of the flow channel 15 and the detection part 13a are capable of having approximately the same height when the interior of the groove part 15 is viewed from the inlet 14. In the sensor 100, the thickness of the base body 10 is made smaller than the depth of the recess 5 so as to ensure that a height of each of the first connection member 21 and the second connection member 22 from the bottom surface of the recess 5 is approximately equal to the depth of the recess 5. When the height of each of the first connection member 21 and the second connection member 22 from the bottom surface of the recess 5 is made larger than the depth of the recess 5, the first partition part 25 and the second partition part 26 of the third base body 2a need processing for making both thinner than other portions thereof. However, by ensuring that the height of each of the first connection member 21 and the second connection member 22 from the bottom surface of the recess 5 is approximately equal to the depth of the recess 5, there is no need for the above processing, thus leading to improved production efficiency.

A planar shape of the recess 5 is, for example, similar to a planar shape of the base body 10, and the recess 5 is slightly larger than the base body 10. More specifically, the recess 5 has such a size that allows formation of a clearance of approximately 100 μm between a side surface of the base body 10 and the inner wall of the recess 5 when the base body 10 is mounted on the recess 5.

(Relationship Between Configurations)

The detection element 3 is fixed to the bottom surface of the recess 5 by a die bond material composed mainly of, for example, an epoxy resin, a polyimide resin, or a silicon resin. The end portion 19e of the extraction electrode 19 and the wiring line 7 are electrically connected to each other by a fine metal wire 27 made of, for example, Au. This is also true for the connection between the end portion 20e of the second extraction electrode 20 and the wiring line 7. Instead of the fine metal wire 27, a conductive adhesive, such as Ag paste, may be used to establish the connection between each of the first extraction electrode 19 and the second extraction electrode 20 and the wiring line 7.

A clearance is formed in a connection portion between each of the first extraction electrode 19 and the second extraction electrode 20 and the wiring line 7. Therefore, damage to the fine metal wire 27 is reducible when the second cover member 2 is stuck to the first cover member 1. The clearance is easily formable by disposing the first through hole 16 and the second through hole 17 in the third base body 2a. By the presence of the first partition part 25 between the first through hole 16 and the groove part 15, it is possible to prevent the specimen liquid flowing through the groove part 15 from entering the clearance formed by the first through hole 16. This contributes to reducing occurrence of a short circuit between the first extraction electrodes 19 due to the specimen liquid. Similarly, by the presence of the second partition part 26 between the second through hole 17 and the groove part 15, it is possible to prevent the specimen liquid flowing through the groove part 15 from entering the clearance formed by the second through hole 17. This makes it possible to reduce occurrence of a short circuit between the second extraction electrodes 20 due to the specimen liquid.

The first partition part 25 is located on the first connection member 21, and the second partition part 26 is located on the second connection member 22. More strictly speaking, the flow channel 15 for the specimen liquid is therefore formed by not only the groove part 15 but also a sidewall of the first connection member 21 close to the groove part 15 and a sidewall of the second connection member 22 close to the groove part 15. From the viewpoint of reducing leakage of the specimen liquid into the clearances respectively formed by the first through hole 16 and the second through hole 17, the first partition part 25 and the second partition part 26 are preferably respectively in contact with an upper surface of the first connection member 21 and an upper surface of the second connection member 22. The sensor 100 is, however, configured to have a clearance between a lower surface of the first partition part 25 and the upper surface of the first connection member 21, and between a lower surface of the second partition part 26 and the upper surface of the second connection member 22. Each of these clearances is, for example, 10-60 μm. Owing to these clearances so formed, even when portions including these clearances are subjected to pressure, for example, when the sensor 100 is held between fingers, the clearances absorb the pressure, thereby preventing the pressure from being directly exerted on the first connection member 21 and the second connection member 22. It is consequently possible to prevent the first vibration space 23 and the second vibration space 24 from being considerably distorted. The specimen liquid usually has a certain degree of viscoelasticity. Therefore, by ensuring that the clearances fall within 10-60 μm, it is difficult for the specimen liquid to enter the clearances. It is also possible to prevent the specimen liquid from leaking into the clearances respectively formed by the first through hole 16 and the second through hole 17.

A width of the first partition part 25 is made wider than a width of the first vibration space 23. In other words, it is configured so that a sidewall of the first partition part 25 is located on the frame body of the first connection member 21. Consequently, even when the first partition part 25 comes into contact with the first connection member 21 due to a pressure from the outside, the first partition part 25 is to be supported by the frame body, thereby reducing deformation of the first connection member 21. For a similar reason, a width of the second partition part 26 needs to be made wider than a width of the second vibration space 24.

(Insulating Member)

The first extraction electrode 19, the second extraction electrode 20, the fine metal wire 27, and the wiring line 7, which are respectively formed by the first through hole 16 and the second through hole 17, and are located in the clearances, are covered with an insulating member 28.

This makes it possible to prevent corrosion of these electrodes and the like. By the presence of the insulating member 28, even when the specimen liquid enters a clearance between the first partition part 25 and the first connection member 21, or a clearance between the second partition part 26 and the second connection member 22, the insulating member 28 dams up the specimen liquid. It is therefore possible to prevent a short circuit between the extraction electrodes due to a leakage of the specimen liquid.

Thus, by accommodating the detection element 3 into the recess 5 of the first cover member 1, the sensor 100 ensures the flow channel 15 extending from the inlet 14 to the detection part 13a, thereby allowing the specimen liquid sucked up from the inlet 14 by capillary action or the like to flow into the detection part 13a. That is, the present embodiment is capable of providing the sensor 100 that includes therein the suction mechanism while employing the thick detection element 3.

EXAMPLES

Examples of the sensor 100 respectively according to the foregoing embodiments, and comparative examples were prepared, and measurement of Hb and HbA1c was made. Then, detection variation of HbA1c was calculated on the basis of the measurement.

Firstly, a specimen liquid was prepared using a certified practical reference material for HbA1c available from General Incorporated Association Reference Material Institute for Clinical Chemistry Standards. This material was used to prepare a reagent whose total Hb concentration was 133 mg/mL and HbA1c level was 10.48% (NGSP value).

Subsequently, the reagent was diluted in a solution containing 100 mM of a succinic acid buffer solution (pH=5) and 0.1% triton X-100 (registered trademark) so as to have a Hb concentration of 0.9 mg/mL. This was then subjected to inversion mixing and left at room temperature for 10 minutes.

Thereafter, the specimen liquid was introduced into the detection part 13a/reference part 13b in the detection element 3 of the sensor 100 by using capillary action.

Then, a difference between a phase immediately (within one second) after introducing the specimen liquid and an average value of phases in a range of 3 to 5 minutes after the introduction was calculated to obtain a detection value (=a phase variation due to binding of HbA1c/a phase variation due to binding of Hb). Here, three detection elements 3 formed using the same wafer were prepared. Their respective detection values were obtained as described above.

A coefficient of variation (CV=σ/AVE) was obtained on the basis of an average value (AVE) of the three detection values calculated in the foregoing manner and a standard deviation (σ).

The following examples and comparative examples were obtained by switching a location of the first detection part D1 and a location of the second detection part D2 between upstream and downstream locations in the flow channel 15 of the sensor 100. The foregoing measurements were made on their respective configurations. Measurement results thereof are presented in Tables 1 and 2.

TABLE 1

| No. | Detection value | AVE (Average value) | σ (Standard deviation) | CV = σ/AVE |
|---|---|---|---|---|
| 1 | 0.645 | 0.679 | 0.031 | 4.5% |
| 2 | 0.705 | | | |
| 3 | 0.685 | | | |

Table 1 presents test results of the examples.

In the sensors of the examples, the first detection part (HbA1c) is located upstream and the second detection part (Hb) is located downstream of the first detection part (HbA1c) in the flow channel. Each of these examples has the reference part 13b described later. The first reference part L1 is disposed upstream of the first detection part D1, and the second reference part L2 is disposed downstream of the second detection part D2. Three sensors respectively according to these examples were prepared, each of which had the configuration as described in the foregoing embodiment, except for the above-mentioned configurations. These examples were subjected to a test according to the foregoing procedure.

Consequently, in the sensors of the example Nos. 1 to 3, an average value of CV was as small as 4.5% as presented in Table 1.

TABLE 2

| No. | Detection value | AVE (Average value) | σ (Standard deviation) | CV = σ/AVE |
|---|---|---|---|---|
| 4 | 0.648 | 0.653 | 0.058 | 8.8% |
| 5 | 0.713 | | | |
| 6 | 0.598 | | | |

Table 2 presents test results of the comparative examples.

In each of the sensors respectively according to the comparative examples, the second detection part (Hb) is located upstream, and the first detection part (HbA1c) is located downstream of the second detection part (Hb) in the flow channel. Each of these comparative examples has the reference part 13b described later. The first reference part L1 is disposed upstream of the second detection part D2, and the second reference part L2 is disposed downstream of the first detection part D1. Three sensors respectively according to these comparative examples were prepared, each of which had the configuration as described in the foregoing embodiment, except for the above-mentioned configuration. These comparative examples were subjected to a test according to the foregoing procedure.

Consequently, in the sensors of the comparative example Nos. 4 to 6, an average value of CV was relatively as large as 8.8% as presented in Table 2.

As described above, the results in Tables 1 and 2 show that measurement variations of the detection values of HbA1c and Hb are reduced by disposing the first detection part D1 having the first ligand LG1 capable of specific binding to HbA1c on the upstream side of the second detection part D2 having the second ligand LG2 capable of specific binding to Hb in the flow channel.

The reason for these results seems to be as follows. That is, when the first detection part D1 is located upstream of the second detection part D2, the first ligand LG1 of the first detection part D1 is capable of specific binding to HbA1c before the second ligand LG2 of the second detection part D2 is specifically bound to HbA1c. This minimizes the influence of the specific binding of the second ligand LG2 of the second detection part D2 located downstream to HbA1c.

(Modifications of Detection Part and Reference Part)

The sensor 100 of the foregoing embodiment may further have one or more reference parts 13b.

Figure 7:
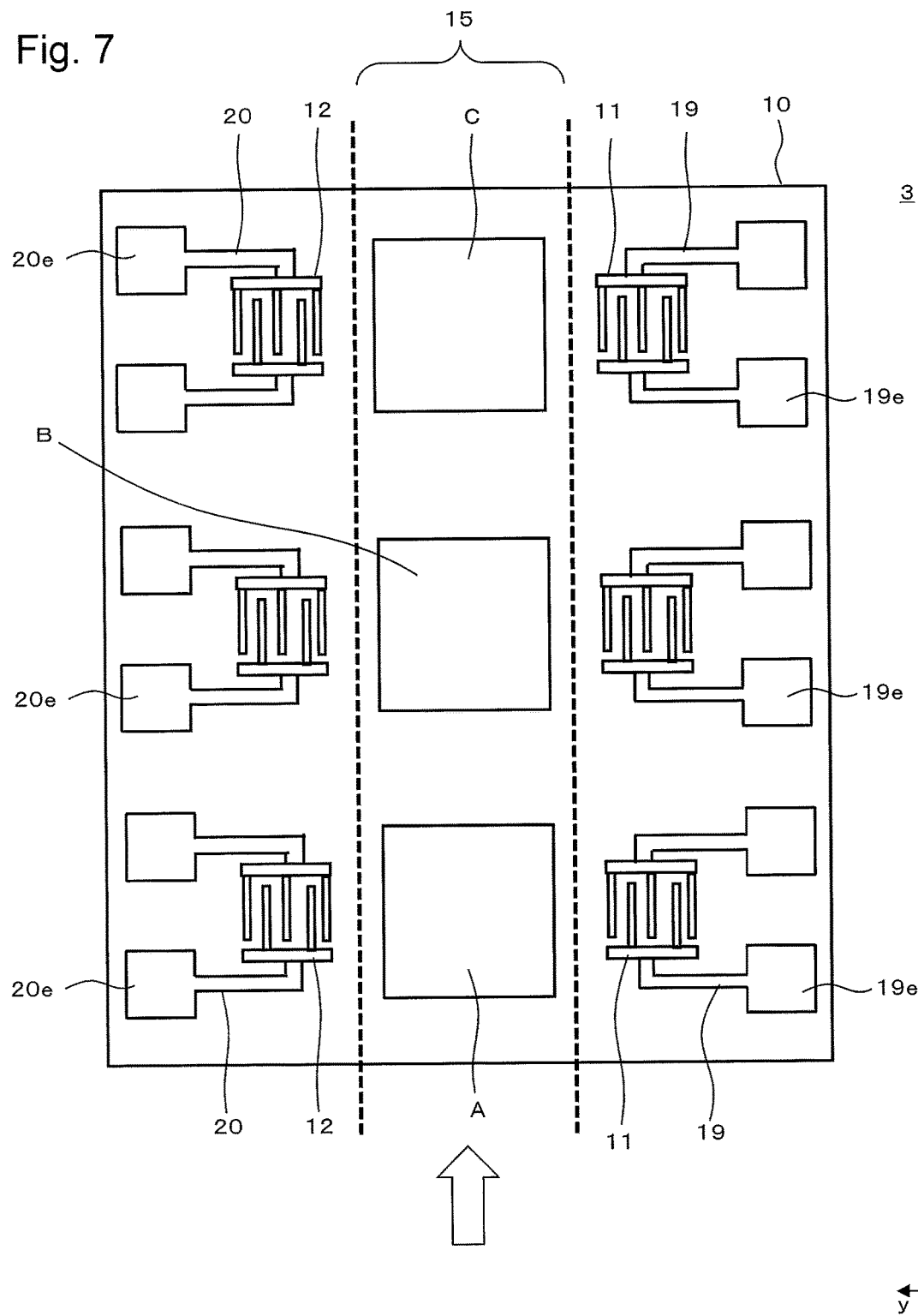
FIG. 7 is a plan view showing a modification of the detection element in FIG. 6.
Figure 8:
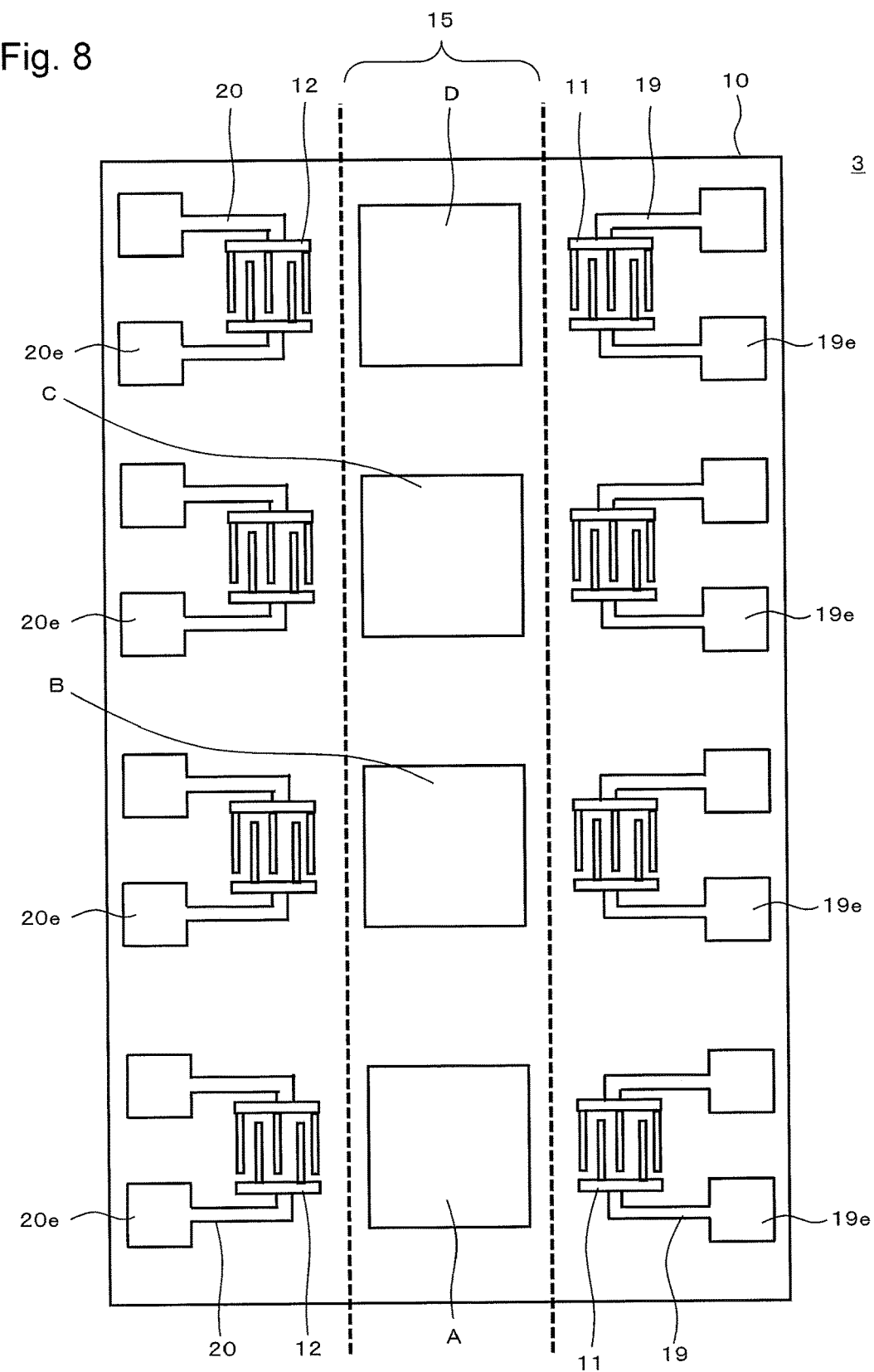
FIG. 8 is a plan view showing a modification of the detection element in FIG. 6.
Figure 9:
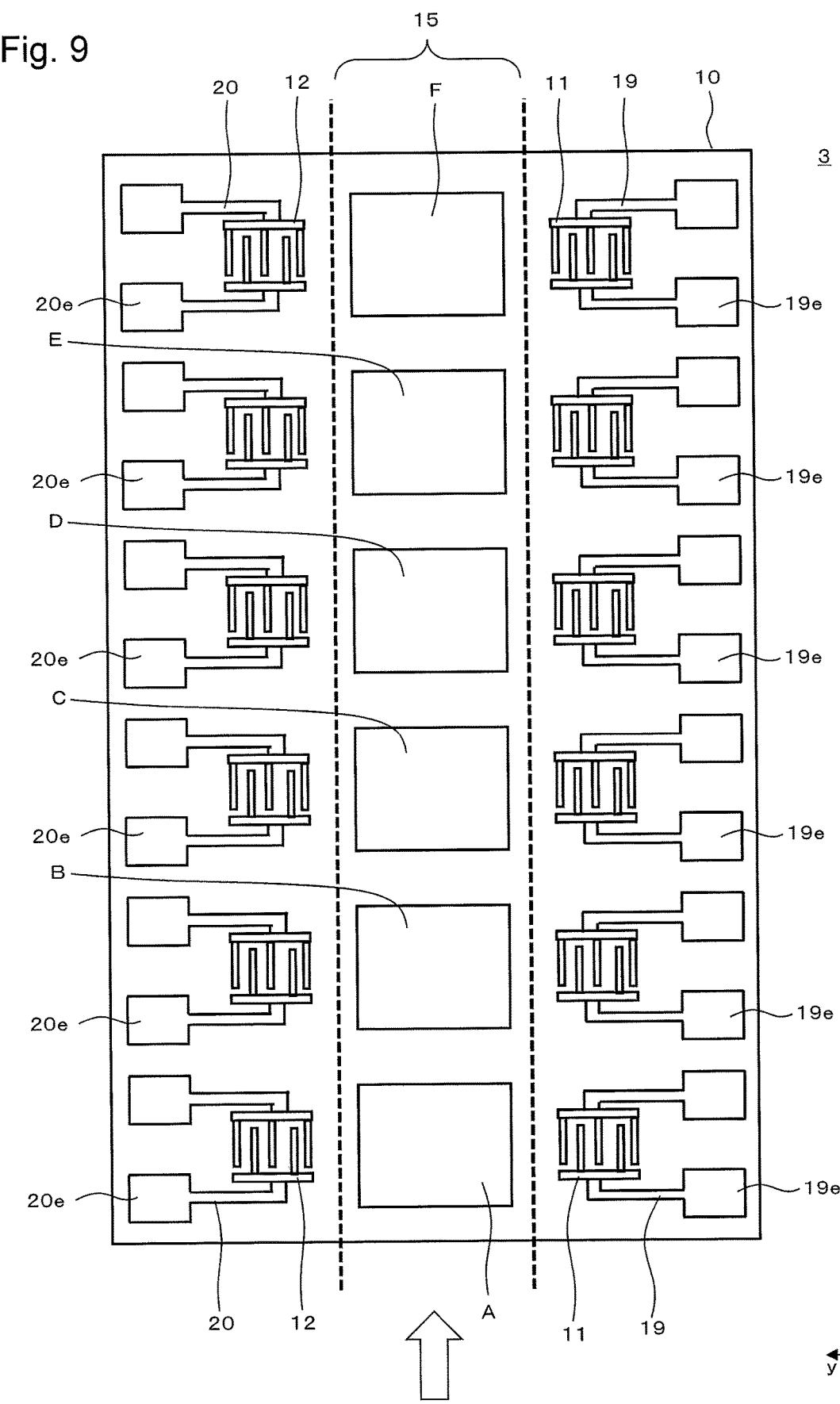
FIG. 9 is a plan view showing a modification of the detection element in FIG. 6.

For example, in FIGS. 7 and 8, when two of reference characters A to D are the foregoing first detection part D1 and second detection part D2, remaining one or two ones may be the reference part 13b.

Here, the reference part 13b is one which is free from the first ligand LG1 and the second ligand LG2 which are capable of specific binding to the first material and the second material in the specimen liquid, respectively. That is, compared to the configuration of the detection part 13a, the configuration of the reference part 13b does not have an antibody or an aptamer composed of nucleic acid and peptide, but has PEG (polyethylene glycol) immobilized to a surface of the metal film.

That is, the reference part 13b is not intended to cause a reaction with the target materials (the first material and the second material) in the specimen liquid. Even when the specimen liquid comes into contact with the reference part 13b, the reference part 13b does not basically cause any binding with the target materials. It is necessary to design so that a material except for the specific target materials in the specimen liquid is less apt to attach the surface of the reference part 13b, as in the surface of the detection part 13a.

Thus, by comparison with a signal in the reference part 13b that does not have the antibody or the aptamer, a signal based on the specific binding to the first material and the second material owing to the antibody or the aptamer in the detection part 13a is accurately detectable, thereby leading to highly reliable measurement.

Examples respectively having configurations different from those of the detection element 3 (configuration example 1) in the foregoing embodiment are sequentially described below.

Configuration Example 2

A detection element 3 shown in FIG. 7 has the detection part 13a and the reference part 13b whose sum is three.

In the present configuration example, the first detection part D1 (A), the second detection part D2 (B), and the first reference part L1 (C) are disposed in order from the upstream side of the flow channel 15. That is, the reference part L1 is disposed downward of the two detection parts 13a.

Accordingly, the first reference part L1 is added as a reference part 13b. Compared to the foregoing configuration example 1, it is possible to reduce influences of nonspecific adsorption, and density and viscosity of a solvent, thus achieving higher accuracy measurements of the target materials. That is, an amount of protein differs depending on the specimen liquid, and therefore, an amount of nonspecific adsorption into the detection part 13a differs between specimen liquids. Hence, by taking a difference in terms of nonspecific adsorption between a phase variation measured at the first reference part L1, and a phase variation measured at the detection part 13a, it is possible to obtain an accurate phase variation with reduced influence of nonspecific adsorption with respect to Hb and HbA1c.

Configuration Example 3

Similarly to the foregoing configuration example 2, a detection element 3 of the configuration example 3 has the detection part 13a and the reference part 13b whose sum is three, as shown in FIG. 7.

In the present configuration example, the first reference part L1 (A), the first detection part D1 (B), and the second detection part D2 (C) are disposed in order from the upstream side of the flow channel 15.

Accordingly, the first reference part L1 is disposed upstream of the two detection parts 13a. Therefore, before a reaction occurs at the detection part 13a (before the amount of each of Hb and HbA1c is decreased), a phase variation due to nonspecific adsorption with respect to the specimen liquid can be measured more accurately at the first reference part L1. This permits measurement with further reduced influence of nonspecific adsorption.

Configuration Example 4

Similarly to the foregoing configuration example 2, a detection element 3 of the configuration example 4 has the detection part 13a and the reference part 13b whose sum is three, as shown in FIG. 7.

In the present configuration example, the first detection part D1 (A), the first reference part L1 (B), and the second detection part D2 (C) are disposed in order from the upstream side of the flow channel 15.

Accordingly, the first reference part L1 is disposed between the first detection part D1 and the second detection part D2, and the first reference part L1 is located close to each of the detection parts D1 and D2. The single reference part 13b is therefore capable of contributing to improvement in measurement accuracy of the two detection parts 13a.

Configuration Example 5

A detection element 3 shown in FIG. 8 has the detection part 13a and the reference part 13b whose sum is four.

In the present configuration example, the first reference part L1 (A), the first detection part D1 (B), the second detection part D2 (C), and the second reference part L2 (D) are disposed in order from the upstream side of the flow channel 15.

Accordingly, the two reference parts L1 and L2 are disposed at positions respectively close to the two detection parts D1 and D2, thus permitting an accurate measurement of a phase variation due to nonspecific adsorption. Additionally, by the presence of the two reference parts 13b, phase variations respectively obtained by them are averaged and evaluated, thereby making it possible to further improve measurement accuracy.

Configuration Example 6

Similarly to the foregoing configuration example 5, a detection element 3 of the configuration example 6 has the detection part 13a and the reference part 13b whose sum is four, as shown in FIG. 8.

In the present configuration example, the first reference part L1 (A), the first detection part D1 (B), the second reference part L2 (C), and the second detection part D2 (D) are disposed in order from the upstream side of the flow channel 15.

Accordingly, the second reference part L2 is disposed upstream of the second detection part D2 and adjacent thereto. It is therefore possible to accurately detect, as a phase variation, a solution state immediately before the second material in the specimen liquid reacts with the second ligand LG2 of the second detection part D2.

Configuration Example 7

Similarly to the foregoing configuration example 5, a detection element 3 of the configuration example 7 has the detection part 13a and the reference part 13b whose sum is four, as shown in FIG. 8.

In the present configuration example, the first detection part D1 (A), the first reference part L1 (B), the second detection part D2 (C), and the second reference part L2 (D) are disposed in order from the upstream side of the flow channel 15.

Accordingly, the reference parts L1 and L2 are respectively disposed close to the detection parts D1 and D2, thus making it possible to accurately measure a phase variation due to nonspecific adsorption.

Configuration Example 8

Similarly to the foregoing configuration example 5, a detection element 3 of the configuration example 8 has the detection part 13a and the reference part 13b whose sum is four, as shown in FIG. 8. The two reference parts 13b are located adjacent to each other.

In the present configuration example, the first detection part D1 (A), the second detection part D2 (B), the first reference part L1 (C), and the second reference part L2 (D) are disposed in order from the upstream side of the flow channel 15.

Accordingly, because the two reference parts 13b are located adjacent to each other, when phase variations respectively obtained by them are averaged and evaluated, it is possible to accurately measure a phase variation due to nonspecific adsorption, thereby further improving measurement accuracy.

Configuration Example 9

Similarly to the foregoing configuration example 5, a detection element 3 of the configuration example 9 has the detection part 13a and the reference part 13b whose sum is four, as shown in FIG. 8. The two reference parts 13b are located adjacent to each other.

In the present configuration example, the first detection part D1 (A), the first reference part L1 (B), the second reference part L2 (C), and the second detection part D2 (D) are disposed in order from the upstream side of the flow channel 15.

Accordingly, the first reference part L1 and the second reference part L2 are located between the first detection part D1 and the second detection part D2. Therefore, the two reference parts 13b are capable of contributing to improvement in measurement accuracy of the two detection parts 13a.

Configuration Example 10

Similarly to the foregoing configuration example 5, a detection element 3 of the configuration example 10 has the detection part 13a and the reference part 13b whose sum is four, as shown in FIG. 8. The two reference parts 13b are located adjacent to each other.

In the present configuration example, the first reference part L1 (A), the second reference part L2 (B), the first detection part D1 (C), and the second detection part D2 (D) are disposed in order from the upstream side of the flow channel 15.

Accordingly, the reference parts 13b are disposed on the upstream side. Therefore, a phase variation due to nonspecific adsorption with respect to the specimen liquid is more accurately detectable in the reference part 13b before a reaction occurs at the detection part 13a. This permits measurement with further reduced influence of nonspecific adsorption.

<Sensor According to Second Embodiment>

A sensor according to the second embodiment of the present invention is described below. In the present embodiment, the description is made using expressions of the second ligand and the second detection part, which are the same as in the foregoing first embodiment, as described later. In the present embodiment, target materials in the second ligand and the second detection part are different from those in the first embodiment. However, their respective descriptions are made using the expression of the second ligand and the second detection part for the sake of convenience.

The sensor according to the second embodiment of the present invention includes a flow channel to permit passage of a specimen liquid, a first detection part having a first ligand that is located in the flow channel and is capable of specific binding to a first material in the specimen liquid, and a second detection part that is located downstream of the first detection part in the flow channel and has a second ligand capable of specific binding to a second material in the specimen liquid. A concentration of the first material is smaller than a concentration of the second material in the specimen liquid.

The sensor of the present embodiment differs from the sensor of the foregoing first embodiment in that the second detection part is not required to be capable of specific binding to the first material. There is a magnitude relation between the concentration of the first material and the concentration of the second material in the specimen liquid.

With this configuration, for example, an anti-Hb antibody capable of specific binding to HbA1c as the first material is usable as the first ligand, and an anti-HbAO antibody capable of specific binding to HbAO as the second material is usable as the second ligand. That is, with the sensor of the present embodiment, even when the first material and the second material are different kinds of materials, an accurate measurement is performable without interaction therebetween. Additionally, even when the concentration of HbA1c as the first material is smaller than the concentration of HbAO as the second material, HbA1c as the first material is accurately detectable at the first detection part on the upstream side without the influence of the second detection part on the downstream side.

Alternatively, for example, an anti-CRP antibody capable of specific binding to CRP (C-reactive protein) as the first material is usable as the first ligand, and an anti-Hb antibody capable of specific binding to Hb as the second material is usable as the second ligand. This case also produces the effects as described above.

The second detection part may be capable of specific binding to the first material.

The configurations of the sensor according to the foregoing first embodiment are appropriately applicable to configurations other than those as described above in the present embodiment. This is also true for the following various forms.

The present invention is not limited to the foregoing embodiments or modifications, and may be carried out in various forms.

For example, the foregoing embodiments have described the cases where the detection element 3 has the two or less detection parts 13a and the two or less reference parts 13b, without limitation thereto. The detection element 3 may be configured to have three or more of either or both thereof. This makes it possible to measure more materials and more accurately measure a certain material. On that occasion, the arrangement of the detection parts 13a and the reference parts 13b is preferably appropriately set according to the foregoing configuration examples in order to more accurately detect a target material.

For example, the configuration having three or more detection parts 13a is described below. A detection part other than the first detection part D1 and the second detection part D2 may be further included. This detection part is located in the flow channel 15 and has other ligand LG (not shown) capable of specific binding to a material except for the first material and the second material in a specimen. This makes it possible to measure more kinds of materials. There needs to be at least one other detection part. When including a plurality of other detection parts, these other detection parts may be disposed sequentially as follows: a third detection part D3, a fourth detection part D4, a fifth detection part D5, . . . . For example, the same other detection parts may be disposed sequentially as follows: the third detection part D3, the third detection part D3, the third detection part D3, . . . . Alternatively, a plurality of other detection parts may be disposed by combining the above ones. Positions of these other detection parts are not particularly limited as long as being located in the flow channel 15. That is, other detection part can be disposed at a desired position with respect to the first detection part D1, the second detection part D2, and the reference part 13b. As a specific example of employing the third detection part D3 as other detection part, there is, for example, a configuration in which the first reference part L1 (A), the first detection part D1 (B), the second detection part D2 (C), the second reference part L2 (D), the third detection part D3 (E), and the third detection part D3 (F) are disposed sequentially from the upstream side of the flow channel 15 in FIG. 9.

The foregoing configuration having these other detection parts is also applicable to the reference part 13b. That is, at least one other reference part except for the first reference part L1 and the second reference part L2 may be further included. That is, at least one other reference part that is located in the flow channel 15 and does not have any ligand capable of specific binding to the first material and the second material and to a material except for the first material and the second material. When including a plurality of other reference parts, the plurality of other reference parts may be disposed sequentially as follows: a third reference part L3, a fourth reference part L4, a fifth reference part L5, . . . . For example, the same other reference parts may be disposed sequentially as follows: the third reference part L3, the third reference part L3, the third reference part L3 . . . . Alternatively, a plurality of other reference parts may be disposed by combining the above ones. Positions of these other reference parts are not particularly limited as long as being located in the flow channel 15. That is, other reference part can be disposed at a desired position with respect to the first detection part D1, the second detection part D2, the first reference part L1, and the second reference part L2. As a specific example of employing the third reference part D3 as other reference part, there is, for example, a configuration in which the first reference part L1 (A), the first detection part D1 (B), the second detection part D2 (C), the second reference part. L2 (D), the third detection part D3 (E), and the third reference part L3 (F) are disposed sequentially from the upstream side of the flow channel 15 in FIG. 9.

As other configuration having three or more detection parts 13a, it may be configured to include the first detection part D1 and the second detection part D2 whose sum is three or more. When including a plurality of the first detection parts D1, the first detection parts D1 are preferably located sequentially from the upstream side. As a specific example, there is, for example, a configuration in which the first reference part L1 (A), the first detection part D1 (B), the first detection part D1 (C), the first detection part D1 (D), the second detection part D2 (E), and the second reference part L2 (F) are disposed sequentially from the upstream side of the flow channel 15 in FIG. 9. When the first detection parts D1 are located sequentially from the upstream side, phase variations respectively obtained by the first detection parts D1 can be averaged and evaluated, thus further improving measurement accuracy.

This is also applicable to the second detection part D2. When including a plurality of the second detection parts D2, the second detection parts D2 are preferably located sequentially from the upstream side. As a specific example, there are, for example, a configuration in which the first reference part L1 (A), the first detection part D1 (B), the second detection part D2 (C), the second detection part D2 (D), the second detection part D2 (E), and the second reference part L2 (F) are disposed sequentially from the upstream side of the flow channel 15 in FIG. 9, and a configuration in which the first reference part L1 (A), the first detection part D1 (B), the first detection part D1 (C), the second detection part D2 (D), the second detection part D2 (E), and the second reference part L2 (F) are disposed sequentially from the upstream side of the flow channel 15 in FIG. 9. When the second detection parts D2 are located sequentially from the upstream side, phase variations respectively obtained by the second detection parts D2 can be averaged and evaluated, thus further improving measurement accuracy.

The foregoing configuration including the first detection part D1 and the second detection part D2 whose sum is three or more is also applicable to the reference part 13b. That is, it may be configured to include the first reference part L1 and the second reference part L2 whose sum is three or more. When including a plurality of the first reference parts L1, the first reference parts L1 are preferably located sequentially from the upstream side. As a specific example, there is, for example, a configuration in which the first reference part L1 (A), the first reference part L1 (B), the first reference part L1 (C), the first detection part D1 (D), the second detection part D2 (E), and the second reference part L2 (F) are disposed sequentially from the upstream side of the flow channel 15 in FIG. 9. With this configuration, phase variations respectively obtained by the first reference parts L1 can be averaged and evaluated, thus further improving measurement accuracy. Similarly, when including a plurality of the second reference parts L2, the second reference parts L2 are preferably located sequentially from the upstream side. As a specific example, there are, for example, a configuration in which the first reference part L1 (A), the first detection part D1 (B), the second detection part D2 (C), the second reference part L2 (D), the second reference part L2 (E), and the second reference part L2 (F) are disposed sequentially from the upstream side of the flow channel 15 in FIG. 9, and a configuration in which the first reference part L1 (A), the first reference part L1 (B), the first detection part D1 (C), the second detection part D2 (D), the second reference part L2 (E), and the second reference part L2 (F) are disposed sequentially from the upstream side of the flow channel 15 in FIG. 9. With these configurations, phase variations respectively obtained by the second reference parts L2 can be averaged and evaluated, thus further improving measurement accuracy.

In the foregoing embodiments, the detection part 13a is made up of the metal film and the aptamer immobilized to the surface of the metal film has been described. For example, when a target material in a specimen reacts with the metal film, the detection part 13a may be made only of the metal film without using the aptamer. Alternatively, a region between the first IDT electrode 11 and the second IDT electrode 12 on the surface of the base body 10 that is a piezoelectric substrate may be used as the detection part 13a, without using the metal film.

For example, though the sensor of the embodiment has been described by exemplifying the SAW (Surface Acoustic Wave) sensor, a measuring cell for use in measurement by a SPR (Surface Plasmon Resonance) apparatus, or a QCM (Quartz Crystal Microbalance) sensor may be used. For example, when using the detection element 3 provided with an optical waveguide in which surface plasmon resonance occurs, for example, a change of optical refraction index in the detection part is to be read. When using the detection element 3 having an oscillator formed on a piezoelectric substrate of quartz, for example, a change in oscillation frequency of the oscillator is to be read.

For example, as the detection element 3, a plurality of kinds of devices may be mounted together on the single base body 10. For example, an enzyme electrode for an enzyme electrode method may be disposed adjacent to an SAW element. This case permits measurement by an enzyme method, in addition to an immunization method using the antibody and the aptamer, thereby increasing the number of items inspectable at a time.

For example, the foregoing embodiments have exemplified the case where the first cover member 1 is made up of the first base body 1a and the second base body 1b, and the second cover member 2 is made up of the third base body 2a and the fourth base body 2b, without limitation thereto. It is possible to use the first cover member 1 in which any pair of these base bodies 1a, 1b, 2a, and 2b are integrated with each other, for example, the first base body 1a and the second base body 1b are integrated with each other.

For example, though the foregoing embodiments have exemplified the case of disposing the single detection element 3, a plurality of the detection elements 3 may be disposed. In this case, the recess 5 may be disposed in each of the detection elements 3, or the recess 5 that is long enough to accommodate all of the detection elements 3 may be formed.

The groove part 15 may be disposed in either one or both of the first cover member 1 and the second cover member 2. For example, the flow channel 15 may be formed by disposing the groove part in both of the first cover member 1 and the second cover member 2. Alternatively, the flow channel 15 may be formed by disposing the groove part in either one of the first cover member 1 and the second cover member 2.

For example, the foregoing embodiments have exemplified the case where the base body 10 is disposed on the first cover member, and the first cover member 1 and the second cover member 2 are connected to each other, without limitation thereto. For example, the flow channel 15 may be formed by directly connecting the cover part to the base body 10.

For example, the foregoing embodiments have exemplified the case where the specimen is in the liquid state (specimen liquid), without limitation thereto. That is, the specimen is not limited to be in the liquid state as long as being measurable with the sensor of the present embodiments. For example, the specimen may be in a gel state or a gas state. The specimen may be one whose state changes, such as one which approaches a solid state from the liquid state in the flow channel 15 (on the detection part 13a).

The invention claimed is:

1. A sensor, comprising:
a flow channel configured to flow a specimen therein;
a first detection part that is located in the flow channel and has a first ligand specifically bindable to a first material in the specimen;
a second detection part that is located downstream of the first detection part in the flow channel and has a second ligand specifically bindable to the first material and a second material in the specimen;
a first electrode located on a first side of the flow channel;
a second electrode located on a second side of the flow channel opposite the first side, wherein the first and second electrodes are configured to detect the first material, and wherein the first detection part is disposed directly between the first and second electrodes;
a third electrode located on the first side of the flow channel;
a fourth electrode located on the second side of the flow channel, wherein the third and fourth electrodes are configured to detect the second material, and wherein the second detection part is disposed directly between third and fourth electrodes;
a first reference part located in the flow channel without the first ligand and the second ligand specifically bindable to the first material and the second material, respectively;
a fifth electrode located on the first side of the flow channel; and
a sixth electrode located on the second side of the flow channel, wherein the fifth and sixth electrodes are configured to provide a reference measurement signal, and wherein the first reference part is disposed directly between the fifth and sixth electrodes.

2. The sensor according to claim 1, wherein a concentration of the first material is smaller than a concentration of the second material in the specimen.

3. The sensor according to claim 1, wherein
the first electrode is configured to generate a surface acoustic wave (SAW) that propagates toward the first detection part; and
the second electrode is configured to receive the SAW after the SAW passes through the first detection part.

4. The sensor according to claim 3, wherein the second detection part is specifically bindable to the first material.

5. The sensor according to claim 1, wherein the second material includes the first material.

6. The sensor according to claim 1, wherein the second material is Hb.

7. The sensor according to claim 1, wherein the first material is HbA1c.

8. The sensor according to claim 1, further comprising:
a second reference part located downstream of the first reference part in the flow channel without the first ligand and the second ligand specifically bindable to the first material and the second material.

9. The sensor according to claim 8, wherein the first reference part is located upstream of the first detection part in the flow channel.

10. The sensor according to claim 9, wherein the second reference part is located upstream of the first detection part in the flow channel.

11. The sensor according to claim 9, wherein the second reference part is located downstream of the first detection part in the flow channel.

12. The sensor according to claim 11, wherein the second reference part is located upstream of the second detection part in the flow channel.

13. The sensor according to claim 11, wherein the second reference part is located downstream of the second detection part in the flow channel.

14. The sensor according to claim 8, wherein the first reference part is located downstream of the first detection part in the flow channel.

15. The sensor according to claim 14, wherein the first reference part is located between the first detection part and the second detection part in the flow channel.

16. The sensor according to claim 14, wherein the first reference part is located downstream of the second detection part in the flow channel.

17. The sensor according to claim 1, further comprising:
at least one other detection part that is located in the flow channel and has other ligand specifically bindable to other material except for the first material and the second material in the specimen.

18. The sensor according to claim 1, comprising a plurality of the first detection parts, the plurality of first detection parts being located sequentially from an upstream side.

19. The sensor according to claim 1, comprising a plurality of the second detection parts, the plurality of second detection parts being located sequentially from an upstream side.

* * * * *